US009421048B2

(12) United States Patent
Lee et al.

(10) Patent No.: US 9,421,048 B2
(45) Date of Patent: Aug. 23, 2016

(54) SUPPORT INSTRUMENT WITH MODULAR INTRAMEDULLARY NAIL

(71) Applicants: Metal Industries Research & Development Centre, Kaohsiung (TW); Pei-Yuan Lee, Kaohsiung (TW)

(72) Inventors: Pei-Yuan Lee, Kaohsiung (TW); Yen-Nien Chen, Koahsiung (TW); Wei-The Chen, Kaohsiung (TW); Wei-Ching Wang, Kaohsiung (TW)

(73) Assignees: Metal Industries Research & Development Centre, Kaohsiung (TW); Pei-Yuan Lee, Kaohsiung (TW)

( * ) Notice: Subject to any disclaimer, the term of this patent is extended or adjusted under 35 U.S.C. 154(b) by 688 days.

(21) Appl. No.: 13/846,344

(22) Filed: Mar. 18, 2013

(65) Prior Publication Data

US 2013/0231666 A1    Sep. 5, 2013

Related U.S. Application Data

(62) Division of application No. 13/152,393, filed on Jun. 3, 2011, now abandoned.

(30) Foreign Application Priority Data

Feb. 10, 2011    (TW) .............................. 100104443 A

(51) Int. Cl.
*A61B 17/72*        (2006.01)
(52) U.S. Cl.
CPC ....... *A61B 17/7283* (2013.01); *A61B 17/7208* (2013.01); *A61B 17/7258* (2013.01)

(58) Field of Classification Search
CPC ...................................... A61B 17/72–17/7291
See application file for complete search history.

(56) References Cited

U.S. PATENT DOCUMENTS

| 4,236,512 A * | 12/1980 | Aginsky .............. A61B 17/746 606/68 |
| 4,457,301 A | 7/1984 | Walker |
| 4,728,333 A | 3/1988 | Masse et al. |
| 5,549,706 A | 8/1996 | McCarthy |
| 6,607,531 B2 | 8/2003 | Frigg |
| 2005/0187627 A1 | 8/2005 | Ralph et al. |
| 2005/0285441 A1 | 12/2005 | Yan |
| 2008/0269750 A1 | 10/2008 | Justin |
| 2008/0294203 A1 * | 11/2008 | Kovach .............. A61B 17/7032 606/308 |

(Continued)

FOREIGN PATENT DOCUMENTS

| CN | 2453862 | 10/2001 |
| CN | 2666362 Y | 12/2004 |

(Continued)

*Primary Examiner* — Eduardo C Robert
*Assistant Examiner* — Nicholas Plionis
(74) *Attorney, Agent, or Firm* — Alan D. Kamrath; Kamrath IP Lawfirm, P.A.

(57) ABSTRACT

A supporting instrument with a modular intramedullary nail includes a plurality of intramedullary nails and a coupling module. Each intramedullary nail is in a form of a long rod and has a coupling portion arranged between two ends of the intramedullary nail and an abutting surface along a longitudinal face of the intramedullary nail. The coupling module is mounted to the coupling portions of the plurality of intramedullary nails for the abutting surfaces of the plurality of intramedullary nails to abut against each other and for assembling the plurality of intramedullary nails.

13 Claims, 15 Drawing Sheets

(56) References Cited

U.S. PATENT DOCUMENTS

2009/0292316 A1   11/2009   Hess
2010/0168858 A1   7/2010   Hardenbrook et al.

FOREIGN PATENT DOCUMENTS

TW   471306 U   1/2002
TW   588643 U   5/2004

* cited by examiner

SUPPORT INSTRUMENT WITH MODULAR INTRAMEDULLARY NAIL

This is a divisional application of U.S. patent application Ser. No. 13/152,393, filed on Jun. 3, 2011, now abandoned.

BACKGROUND OF THE INVENTION

1. Field of the Invention

The present invention relates to a support instrument with an intramedullary nail and, more particularly, to a support instrument with a modular intramedullary nail able to adjust the number of modular intramedullary nails according to dimensions of the medullary cavity of a bone.

2. Description of the Related Art

Generally, the way to treat a patient with a fractured long bone is to insert an intramedullary nail into its medullary cavity to bridge a defect of the fractured long bone for the bone to re-grow and recover in a short period of time.

Referring to FIG. 1, a conventional intramedullary nail disclosed by a Taiwan Patent titled as "Improved Structure of Bone Medulla Internal Nail" with Publication No. 471306 is shown and numbered as "9." The intramedullary nail 9 is in a form of a curved cylinder with an adjusting device 91 for adjustment in a position of the intramedullary nail 9 relative to a medullary cavity wherein the intramedullary nail 9 is disposed. Thus, a defect of a deficient bone having the medullary cavity is provided with stabilization and reinforcement, and the deficient bone can re-grow and recover in a short period of time. When the intramedullary nail 9 is used, a hole communicating with the medullary cavity has to be formed at an end of the deficient bone for the intramedullary nail 9 to be inserted into the medullary cavity. Then screws 92 are used to respectively fix two ends of the intramedullary nail 9 in the medullary cavity firmly.

However, with this kind of intramedullary nail 9, hospitals have to prepare and store intramedullary nails 9 in various sizes for patients with different builds or affected parts since the dimensions of every single intramedullary nail 9 are constant. Therefore, the conventional intramedullary nail 9 may lead to difficulty in reserve management for the hospitals and manufacturers.

Due to the above drawback of the intramedullary nail 9, some other kinds of intramedullary nails, such as the one disclosed by a Taiwan Patent titled as "Multi-Staged Internal Locking Type Internal-Bone Nailing Device" with Publication No. 588643 and shown in FIG. 2, are proposed. Referring to FIG. 2, the intramedullary nail numbered as "8" includes a distal end fixer 81, at least one mid rod 82, and a base end fixer 83. The distal end fixer 81 has a connector 811, with each of the mid rods 82 having two connectors 821 at two ends thereof, and the connectors 811, 821 able to couple with each other. The connector 811 of the distal end fixer 81 is coupled with a connector 821 of a mid rod 82, and the other connector 821 of the mid rod 82 is coupled with the base end fixer 83 or a connector 821 of another mid rod 82. Thus, the intramedullary nail 8 constructed by the distal end fixer 81, at least one mid rod 82, and base end fixer 83 can provide a variable length by changing the number of the at least one mid rod 82. As a result, the length of the intramedullary nail 8 can be adjusted during operation of the deficient bone. Therefore, the reserve management for the intramedullary nail 8 is easy since sizes of the mid rods 82 constructing most parts of the intramedullary nail 8 are identical.

Nevertheless, the connectors 811, 821 of the intramedullary nail 8 easily become structural weaknesses when the intramedullary nail 8 is inserted inside the medullary cavity. Besides, since both of the distal end fixer 81 and mid rod 82 are in the form of a straight cylinder, the curvature of the intramedullary nail 8 is limited and the intramedullary nail 8 may not perfectly fit the medullary cavity when the straight cylinder is too long. Alternately, there may be too many structural weaknesses formed by the connectors 821 when the straight cylinder is too short.

Moreover, a diameter of the cross-sectional view of the intramedullary nail 8 is still unchangeable although the intramedullary nail 8 is an assembly of the distal end fixer 81, at least one mid rod 82, and base end fixer 83. Furthermore, an added or reduced length of the intramedullary nail 8 can only be a multiple of the length of the mid rod 82, which may result in a total length of the intramedullary nail 8 over a suitable length for the medullary cavity. In this situation, only drawing out bone medulla to deepen the medullary cavity for the intramedullary nail 8 is an effective way, and this operation may further hurt the patient.

In light of this, it is desired to improve the conventional intramedullary nail.

SUMMARY OF THE INVENTION

It is therefore the primary objective of this invention to provide a support instrument with a modular intramedullary nail, which can construct a size-variable support instrument by a plurality of modular intramedullary nails to fit patients with different builds or affected parts.

Another objective of this invention is to provide a support instrument with a modular intramedullary nail, which is integrally formed in a longitudinal direction to provide a support instrument with enough structural strength.

Still another object of this invention is to provide a support instrument in a suitable shape corresponding to a medullary cavity designed to be inserted to achieve an easy insertion.

The invention discloses a supporting instrument with a modular intramedullary nail. The supporting instrument comprises a plurality of intramedullary nails and a coupling module. Each of the plurality of intramedullary nails is in a form of a long rod and has a coupling portion arranged between two ends of each intramedullary nail and an abutting surface along a longitudinal face of each intramedullary nail. The coupling module is mounted to the coupling portions of the plurality of intramedullary nails for the abutting surfaces of the plurality of intramedullary nails to abut against each other and assembles the plurality of intramedullary nails.

Furthermore, the coupling portion is in a form of a through hole penetrating the longitudinal face of each intramedullary nail, and the coupling module is an insertion pin.

Furthermore, the coupling portion is in a form of a groove formed on the longitudinal faces of each intramedullary nail, and the coupling module is a C-shaped hook or a ring.

The invention also discloses an intramedullary nail, with the intramedullary nail comprising a body and a coupling portion. The body is in a form of a long rod and has an abutting surface and two ends, with the abutting surface extending along a longitudinal face of the body for abutting against the abutting surface of another intramedullary nail. The coupling portion is arranged between the two ends, and the coupling portion is a through hole or a groove.

BRIEF DESCRIPTION OF THE DRAWINGS

The present invention will become more fully understood from the detailed description given hereinafter and the accompanying drawings which are given by way of illustration only, and thus are not limitative of the present invention, and wherein.

Figure 1:
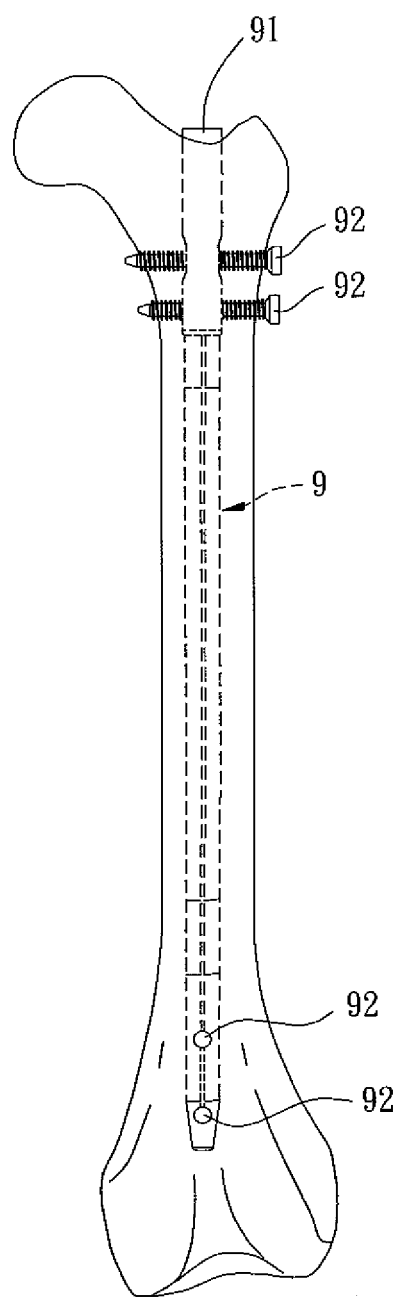
FIG. 1 shows a conventional intramedullary nail.
Figure 2:
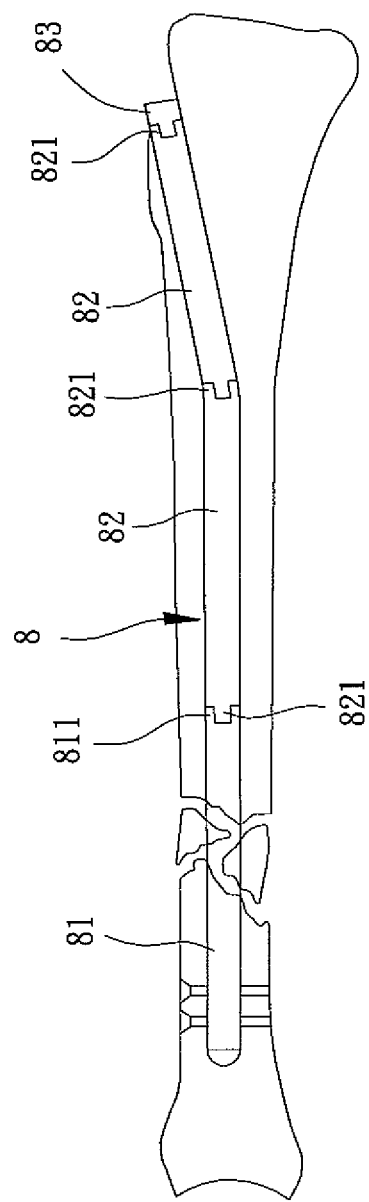
FIG. 2 shows another conventional intramedullary nail.

In the various figures of the drawings, the same numerals designate the same or similar parts. Furthermore, when the terms "first", "second", "third", "inner", "outer", "top", "bottom" and similar terms are used hereinafter, it should be understood that these terms refer only to the structure shown in the drawings as it would appear to a person viewing the drawings, and are utilized only to facilitate describing the invention.

DETAILED DESCRIPTION OF THE INVENTION

Figure 3:
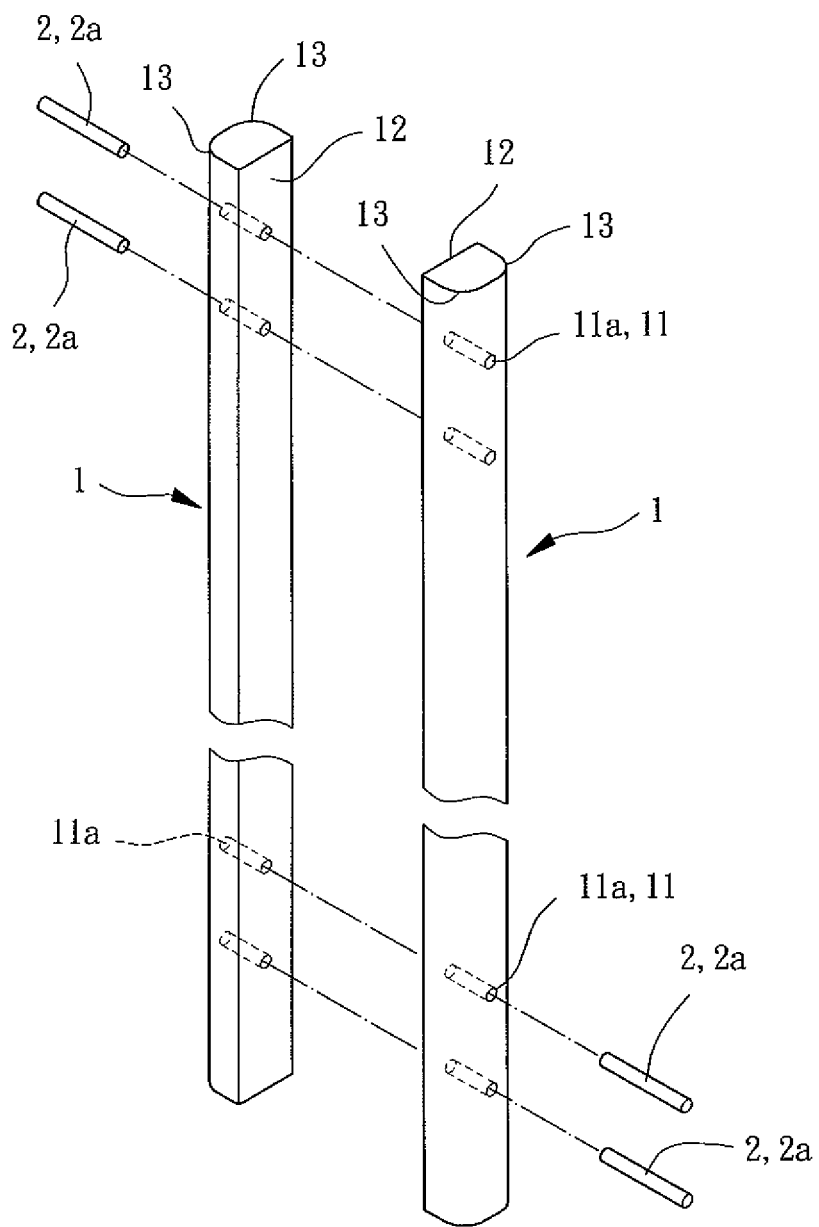
FIG. 3 shows an exploded perspective view of a support instrument with a modular intramedullary nail according to a first embodiment of the invention before bent.

Referring to FIG. 3, a perspective view of a first embodiment of a support instrument with modular intramedullary nail is shown. The support instrument includes a plurality of intramedullary nails 1 and at least one coupling module 2, with the at least one coupling module 2 coupled with the plurality of intramedullary nails 1 to link any adjacent two of the plurality of intramedullary nails 1.

The intramedullary nail 1 is in the form of a long rod and has at least one coupling portion 11 arranged between two ends of the intramedullary nail 1 and an abutting surface 12 along a longitudinal face of the intramedullary nail 1 that extends in a longitudinal direction thereof. The number of the plurality of intramedullary nails 1 may be two, with the abutting surfaces 12 thereof abutting against each other and the coupling module 2 firmly coupling the two intramedullary nails 1 together. Thus, the support instrument can provide an increased cross-sectional area with enhanced structural strength. In the present embodiment, the intramedullary nail 1 is preferably made of implantable stainless steel, with the coupling portion 11 in the form of a through hole 11a penetrating the longitudinal face of the intramedullary nail 1 and extending in a direction perpendicular to the abutting surface 12.

The coupling module 2 is mounted to the coupling portions 11 of two of the two intramedullary nails 1. In this embodiment, the coupling module 2 can be of at least one insertion pin 2a, and each insertion pin 2a has a length equal to or smaller than the total of lengths of aligned through holes 11a of the two intramedullary nails 1. Thus, each insertion pin 2a can be firmly received inside the aligned through holes 11a of the two assembled intramedullary nails 1 without protruding out from outer surfaces of the assembly of the two intramedullary nails 1.

Figure 4:
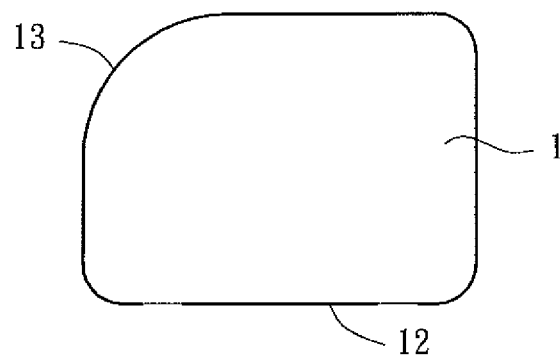
FIG. 4 shows a cross-sectional view of a sample of the support instrument with a modular intramedullary nail.
Figure 5A:
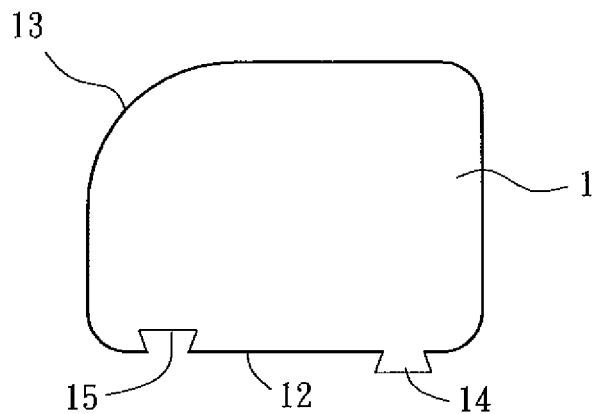
FIG. 5a shows a cross-sectional view of another sample of the support instrument with a modular intramedullary nail.
Figure 5B:
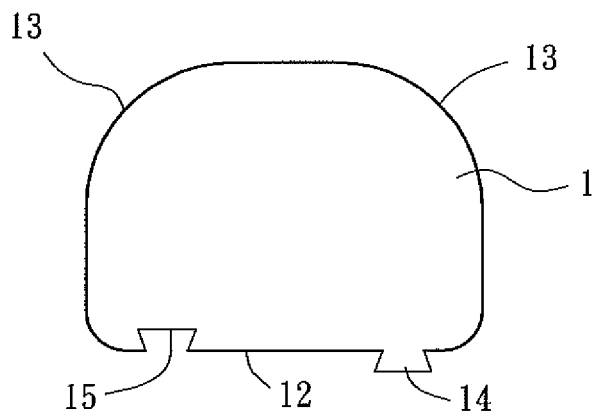
FIG. 5b shows a cross-sectional view of still another sample of the support instrument with a modular intramedullary nail.

In addition, cross-sectional view of each intramedullary nail 1 assembled by the through holes 11a and insertion pin 2a is preferably one of the following three types. Referring to FIG. 4, the first type of the intramedullary nail 1 has a cross-sectional view in the shape of a rectangle with a corner thereof away from the abutting surface 12 being pared off to form a round face 13. Thus, outer surfaces of the assembled intramedullary nails 1 are smooth to avoid hurting the tissues on the inner surface of the medullary cavity. Referring to FIG. 3, the second type of the intramedullary nail 1 has a cross-sectional view in the shape of a rectangle with two corners thereof away from the abutting surface 12 being pared off to form two round faces 13 respectively to further smoothen the outer surfaces of the assembled intramedullary nails 1. Referring to FIGS. 5a and 5b, the third type of the intramedullary nail 1 has a rib 14 and a groove 15 on the abutting surface 12 for the rib 14 of one of the intramedullary nails 1 to insert into the groove 15 of the other one of the intramedullary nails 1 to enhance the engagement between these two intramedullary nails 1. Preferably, in a peripheral direction of each intramedullary nail 1, a distal end of the rib 14 away from the abutting surface 12 is wider than a root end of the rib 14 connecting with the abutting surface 12, a bottom end of the groove 15 is wider than an opening end of the groove 15, and the width of the distal end of the rib 14 is larger than that of the opening end of the groove 15. Accordingly, the two intramedullary nails 1 of the third type can be assembled by oppositely moving in the direction with the rib 14 and groove 15 extending with the rib 14 slidingly received inside the groove 15. Thus, the engagement between the two intramedullary nails 1 is enhanced, since the rib 14 cannot be directly removed from the opening end of the groove 15.

Figure 6:
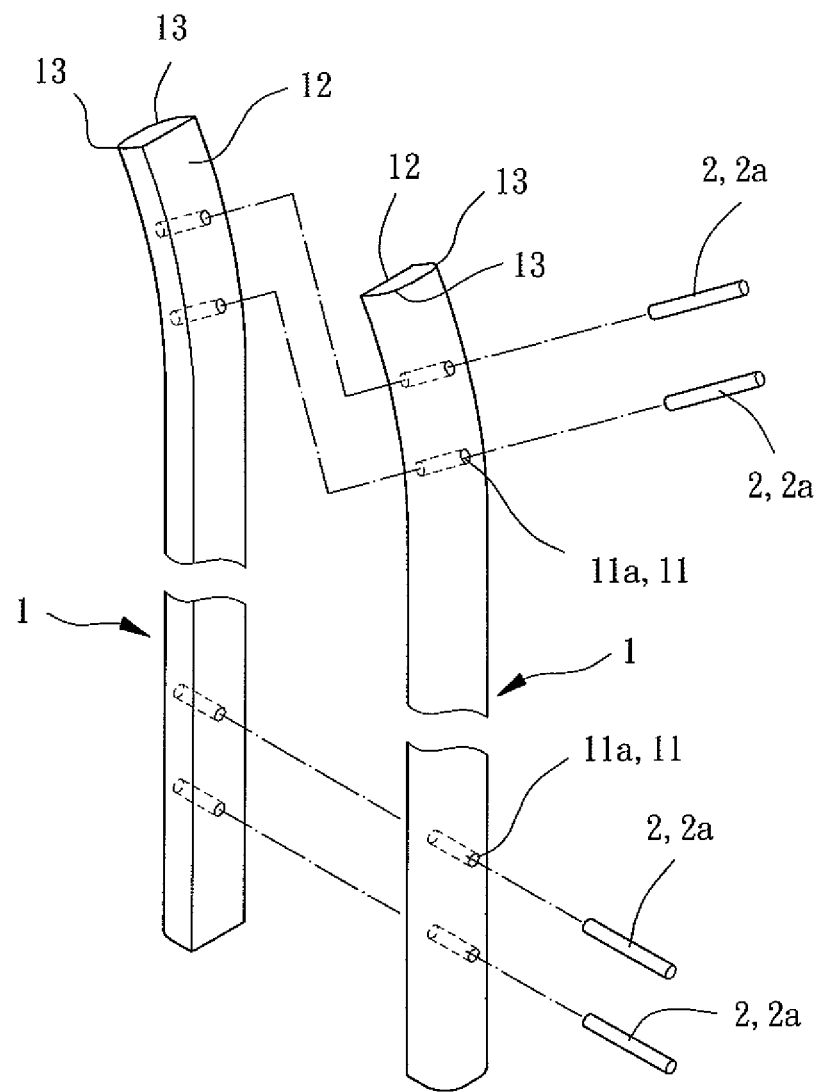
FIG. 6 shows an exploded perspective view of the support instrument with a modular intramedullary nail according to the first embodiment of the invention after bent.
Figure 7:
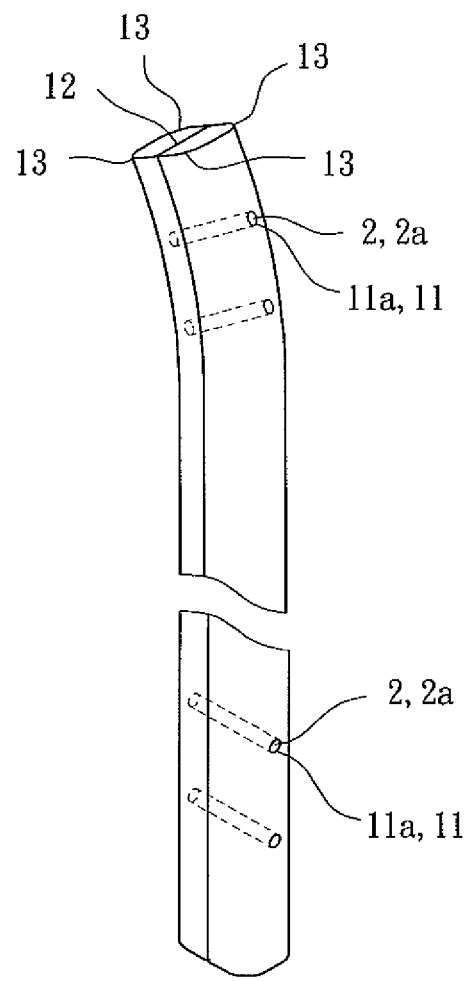
FIG. 7 shows a perspective view of the support instrument with a modular intramedullary nail according to the first embodiment of the invention after assembled.

In order to illustrate the processes in use of the present support instrument in the following, two of the intramedullary nails 1 of the second type are taken as an example. Please refer to FIGS. 6 and 7. A medical operator may obtain the necessary information of the support instrument of the present invention such as the route and caliber of the medullary cavity by the x-ray of a long bone having the medullary cavity, and decides the number of the plurality of intramedullary nails 1 according to the obtained information. When plural intramedullary nails 1 are used, each of the intramedullary nails 1 can be bent to suit the route of the medullary cavity. Then, the bent intramedullary nails 1 are abutted against each other by the abutting surface 12 and firmly assembled by the at least one coupling module 2, with the number of the at least one coupling module 2 preferably corresponding to the number of the at least one coupling portion 11. It is apparent that the intramedullary nails 1 can be assembled first, and then the assembled intramedullary nails 1 can be bent to suit the route of the medullary cavity. Accordingly, the sectional area of the support instrument constructed by the plural intramedullary nails 1 and the at least one coupling module 2 matches the caliber of the medullary cavity. However, the coupling module 2 can be absent if only one intramedullary nail 1 is used.

Referring to FIG. 7 again, in the present embodiment, the coupling module 2 and coupling portion 11 are implemented by plural insertion pins 2a and plural through holes 11a in which the insertion pins 2a are disposed, and the engagement between the intramedullary nails 1 is firm and easy to complete. Besides, the hurt to the tissues on the inner surface of the medullary cavity caused during the operation of insertion of the support instrument can be greatly avoided since the outline of cross-sectional views of the support instrument constructed by the plural intramedullary nails 1 and coupling module 2 is smooth due to the outward-facing round face 13 of each intramedullary nail 1.

Figure 10:
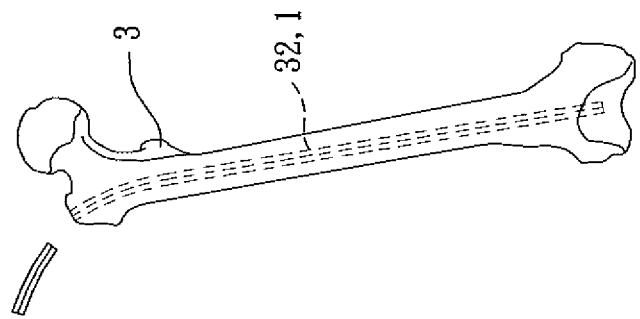
FIG. 10 shows a side view of the support instrument with a modular intramedullary nail according to the first embodiment of the invention of a third step during insertion.
Figure 9:
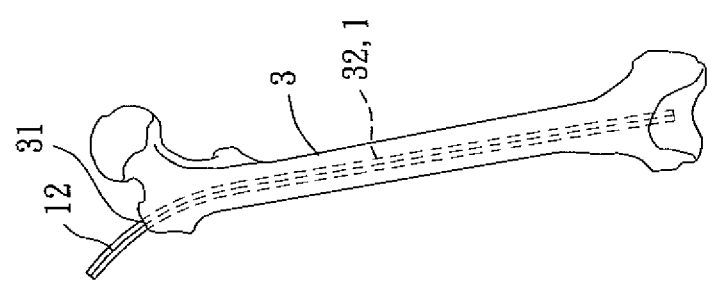
FIG. 9 shows a side view of the support instrument with a modular intramedullary nail according to the first embodiment of the invention of a second step during insertion.
Figure 8:
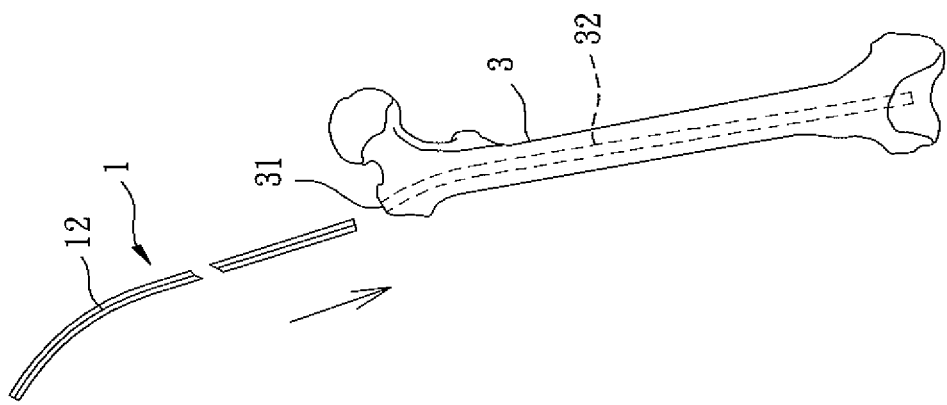
FIG. 8 shows a side view of the support instrument with a modular intramedullary nail according to the first embodiment of the invention of a first step during insertion.

Please refer to FIGS. 8, 9, and 10. The support instrument constructed by the bent intramedullary nails 1 and coupling module 2 is then driven to pass through a hole 31 of a long bone 3, which communicates a medullary cavity 32 and the outside of the long bone 3, into the medullary cavity 32 of the long bone 3. Finally, a part of the support instrument outside the medullary cavity 32 can be cut off after an end of the support instrument in the medullary cavity 32 abuts against the bottom of the medullary cavity 32.

Accordingly, the support instrument formed by the intramedullary nails 1 in the bent shape may perfectly match the route of the medullary cavity 32 and can be inserted into the medullary cavity 32 smoothly without hurting the tissues on the inner surface thereof. Furthermore, the structural strength of each intramedullary nail 1 is high since the intramedullary nail 1 is integrally formed, and the assembled intramedullary nails 1 can further enhance the anti-twist performance of the whole support instrument. Therefore, the present support instrument with a modular intramedullary nail 1 not only is suitable for medullary cavities with various dimensions, but provides high structural strength to upgrade safety in use.

Particularly, the length of each intramedullary nail 1 is long enough for the medical operator to cut off, so that time for estimating the necessary length of the support instrument and dispatching a suitable conventional nail can be omitted. It should be noted that the support instrument of this invention can provide a supporter with an exact and suitable length for the medullary cavity without further deepening the medullary cavity and hurting the tissues on the inner surface of the medullary cavity. Thereby, the present invention can provide simplified processes in operation and, thus, reduce operation time, and the treatment effectiveness is also improved.

Figure 11:
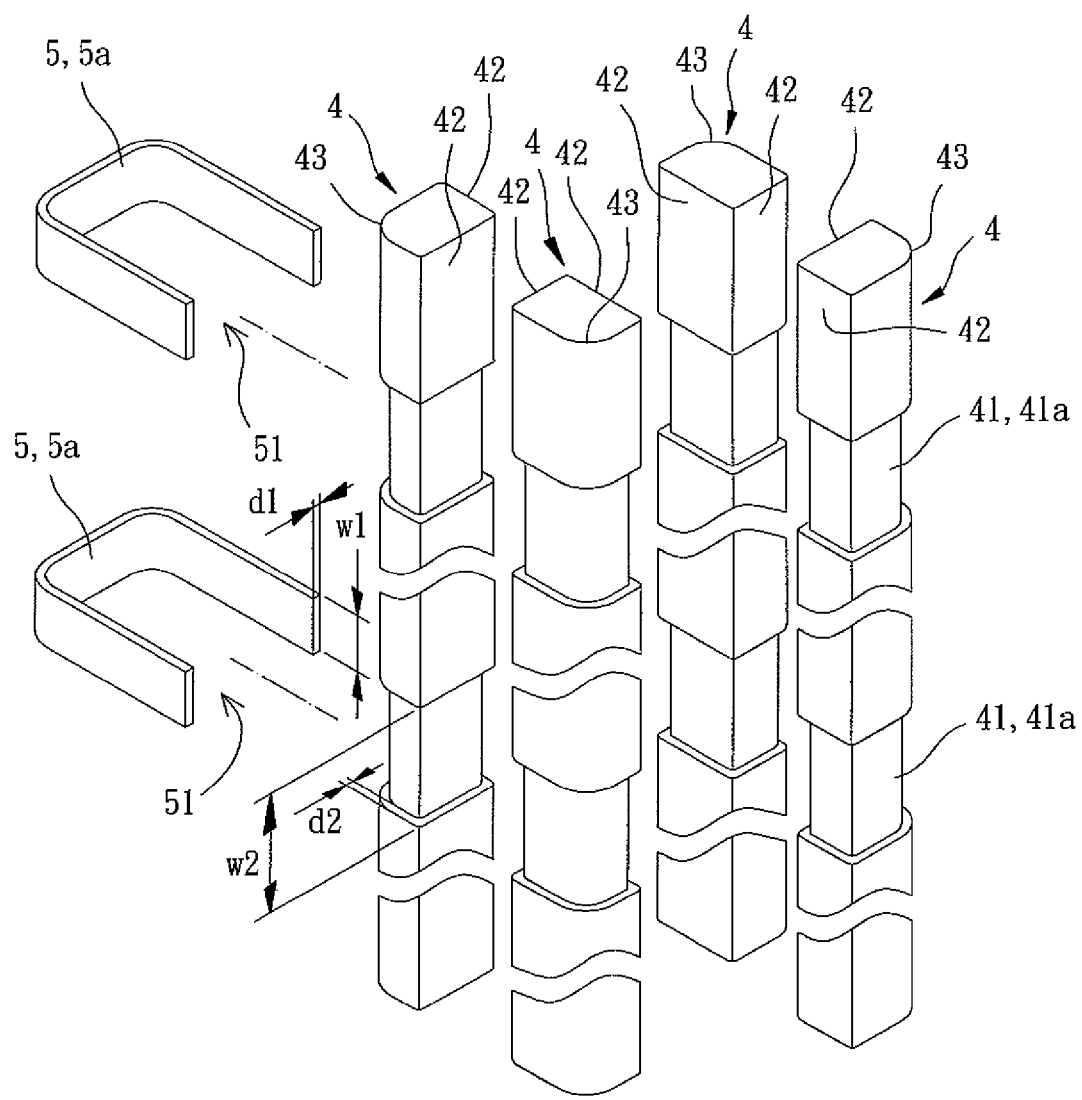
FIG. 11 shows an exploded perspective view of a support instrument with a modular intramedullary nail according to a second embodiment of the invention.

Referring to FIG. 11, an exploded perspective view of a second embodiment of the present invention is illustrated, which is a support instrument including at least one intramedullary nail 4 and at least one coupling module 5. The at least one coupling module 5 is coupled with the at least one intramedullary nail 4 to link any adjacent two of the intramedullary nails 4.

The intramedullary nail 4 is in the form of a long rod and has at least one coupling portion 41 arranged between two ends of the intramedullary nail 4 and a plurality of abutting surfaces 42 along longitudinal faces of the intramedullary nail 4 that extend in a longitudinal direction thereof. Therefore, the number of the at least one intramedullary nail 4 can be a single if the caliber of the medullary cavity in which the support instrument will be inserted is small, and that of the at least one intramedullary nail 4 can be plural if the caliber is large. For example, the number of the plurality of intramedullary nails 4 may be two or four, with the abutting surfaces 42 thereof abutting against each other and the with coupling module 5 firmly coupling the two or four intramedullary nails 4 together. Thus, the support instrument can provide an increased cross-sectional area with enhanced structural strength. Preferably, the assembled intramedullary nails 4 may have the same dimensions while there may be various kinds of intramedullary nails 4 for users to select. Thus, various sectional areas of the support instrument can be provided by a changeful number or size of the assembled intramedullary nails 4. In the present embodiment, the intramedullary nail 4 is preferably made of implantable stainless steel, with the coupling portion 41 in the form of a groove 41a formed on the longitudinal faces of the intramedullary nail 4. Although the coupling portion 41 in this embodiment is in the form of an annular groove, the groove 41a can be formed on all the longitudinal faces of the intramedullary nail 4 except the abutting surfaces 42.

The coupling module 5 is mounted to the coupling portions 41 of plural intramedullary nails 4. In this embodiment, the coupling module 5 can be of at least one hook 5a, and each hook 5a is a C-shaped hook and has an opening 51. A thickness "d1" between an inner face and an outer face of the hook 5a is equal to or smaller than a depth "d2" of the groove 41a of each of the plural intramedullary nails 4. Thus, the hook 5a can be received in the groove 41a without protruding from the outer surfaces of the plural intramedullary nails 4. Furthermore, a width "w1" of the hook 5a is preferably smaller than a width "w2" of the groove 41a of each of the plural intramedullary nails 4, and the hook 5a can still firmly couple with and be received in the grooves 41a even if the plural intramedullary nails 4 are bent. Besides, two lateral arms of the C-shaped hook 5a defining the opening 51 can be bent by a device in the form of a stapling machine to efficiently couple within the grooves 41a, and thus firmly assembles the plural intramedullary nails 4 and the coupling modules 5.

Figure 12:
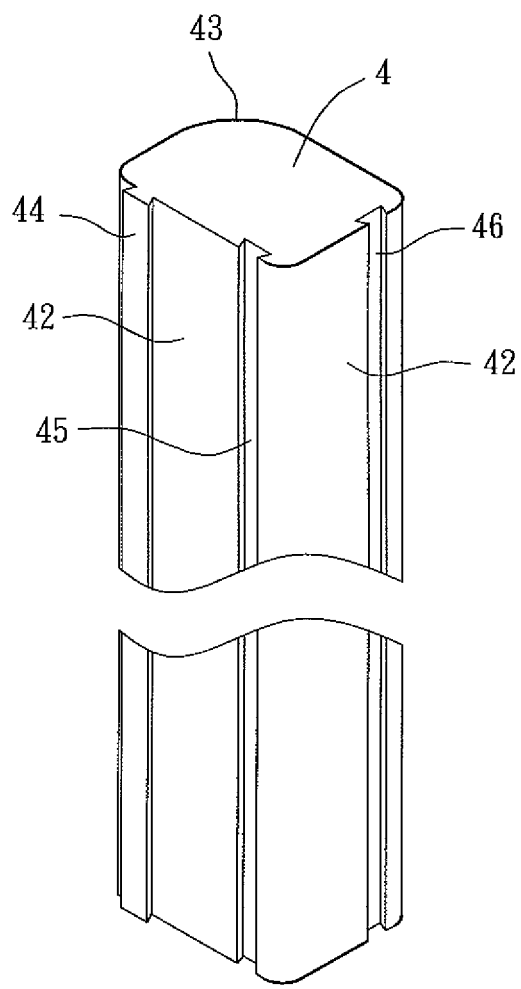
FIG. 12 shows a detailed perspective view of an intramedullary nail according to the second embodiment of the invention.
Figure 13A:
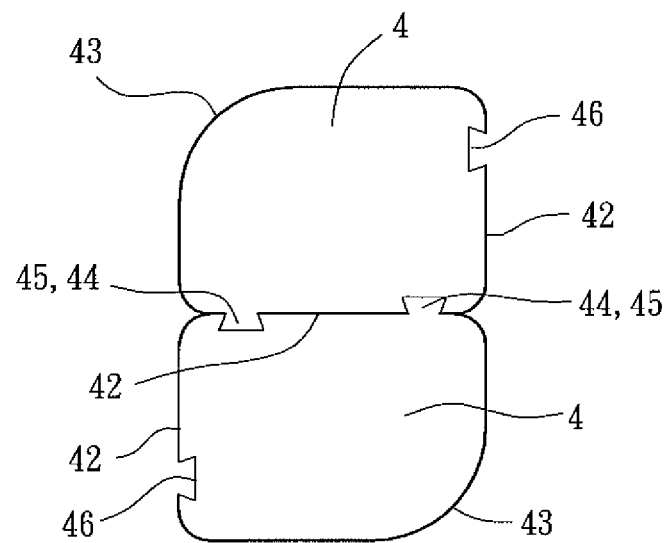
FIG. 13a shows a cross-sectional view of a sample of the support instrument having two intramedullary nails according to the second embodiment of the invention.
Figure 13B:
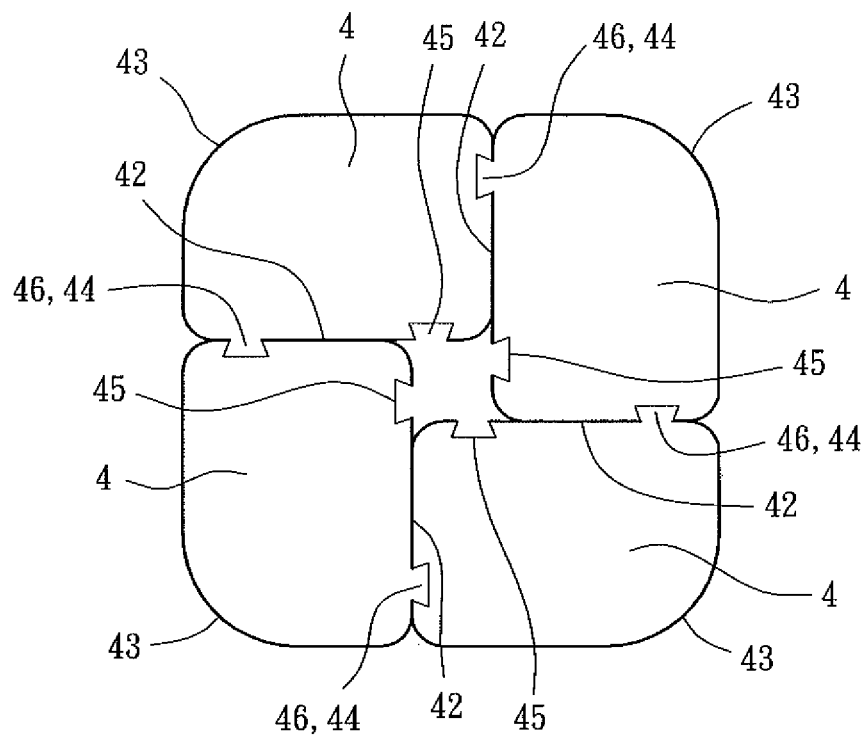
FIG. 13b shows a cross-sectional view of a sample of the support instrument having four intramedullary nails according to the second embodiment of the invention.

In addition, cross-sectional view of each one of the assembled intramedullary nails 4 assembled by the grooves 41a and hook 5a is preferably one of the following two types. Referring to FIG. 11, the first type of the intramedullary nail 1 has a cross-sectional view in the shape of a rectangle with each of two adjacent longitudinal faces defined as an abutting surface 42 and a corner away from these two abutting surfaces 42 being pared off to form a round face 43. Thus, outer surfaces of the assembled intramedullary nails 1 are smooth to avoid hurting the tissues on the inner surface of the medullary cavity. Referring to FIG. 12, the second type of the intramedullary nail 4 has a rib 44, a first groove 45 on one of the abutting surfaces 42 and has a second groove 46 on the other abutting surface 42. Referring to FIG. 13a, when two of the intramedullary nails 4 are assembled, the two abutting surface 42 having the rib 44 and the first groove 45 abut against each other for the ribs 44 to insert into the grooves 45 to enhance the engagement between these two intramedullary nails 4. Referring to FIG. 13b, when four of the intramedullary nails 4 are assembled, the rib 44 of any one of the intramedullary nails 4 couples with the second groove 46 of an adjacent one of them, with the first groove 45 disposed inside an assembly constructed by the four intramedullary nails 4 to reduce the roughness of outer surfaces of the assembly. Moreover, the designs of the rib 44, first groove 45, and second groove 46 can be in the same way of the rib 14 and groove 15 of the first embodiment, and thus the engagement between the intramedullary nails 4 is enhanced since the rib 44 cannot be directly removed from an opening end of the first groove 45 or second groove 46.

Figure 14:
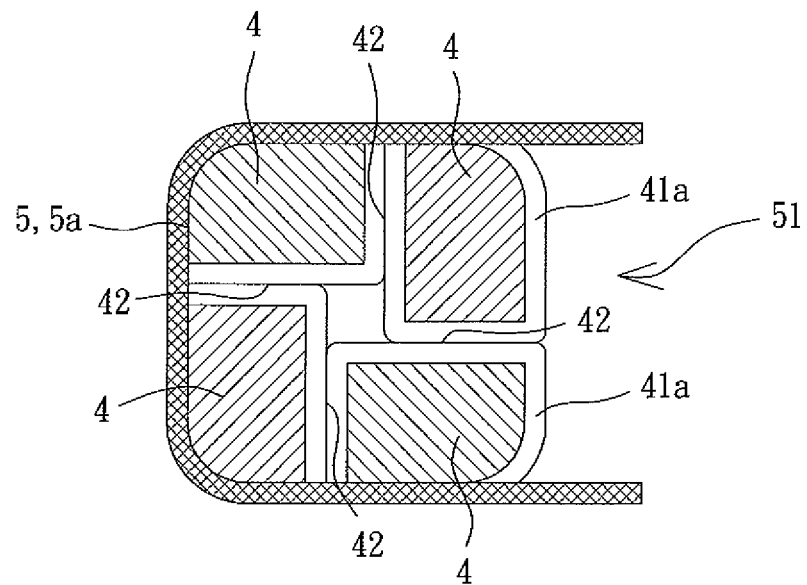
FIG. 14 shows a cross-sectional view of the support instrument of a first assembling step by a C-shaped hook.
Figure 15:
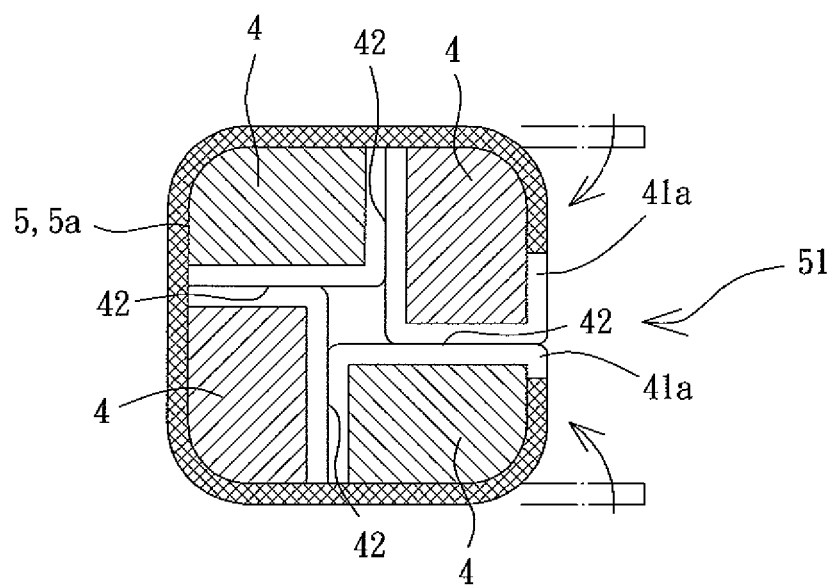
FIG. 15 shows a cross-sectional view of the support instrument of a second assembling step by the C-shaped hook.

Referring to FIGS. 14 and 15, in order to illustrate the processes in use of the present support instrument in the following, four of the intramedullary nails 4 of the second type are taken as an example. However, the number of the at least one intramedullary nail 4 can also be one or two. The processes in operation using the second embodiment of the present invention are similar to those of the first embodiment, and the primary difference between the processes of these two embodiments lies in the engaging operation of the coupling modules 5. Preferably, the grooves 41a of the plural intramedullary nails 4 are in alignment when the intramedullary nails 4 are disposed abreast. Then, the hook 5a surrounds a neck jointly formed by bottoms of the grooves 41a before the two lateral arms of the hook 5a are bent for the hook 5a to firmly clasp all the plural intramedullary nails 4.

Figure 16:
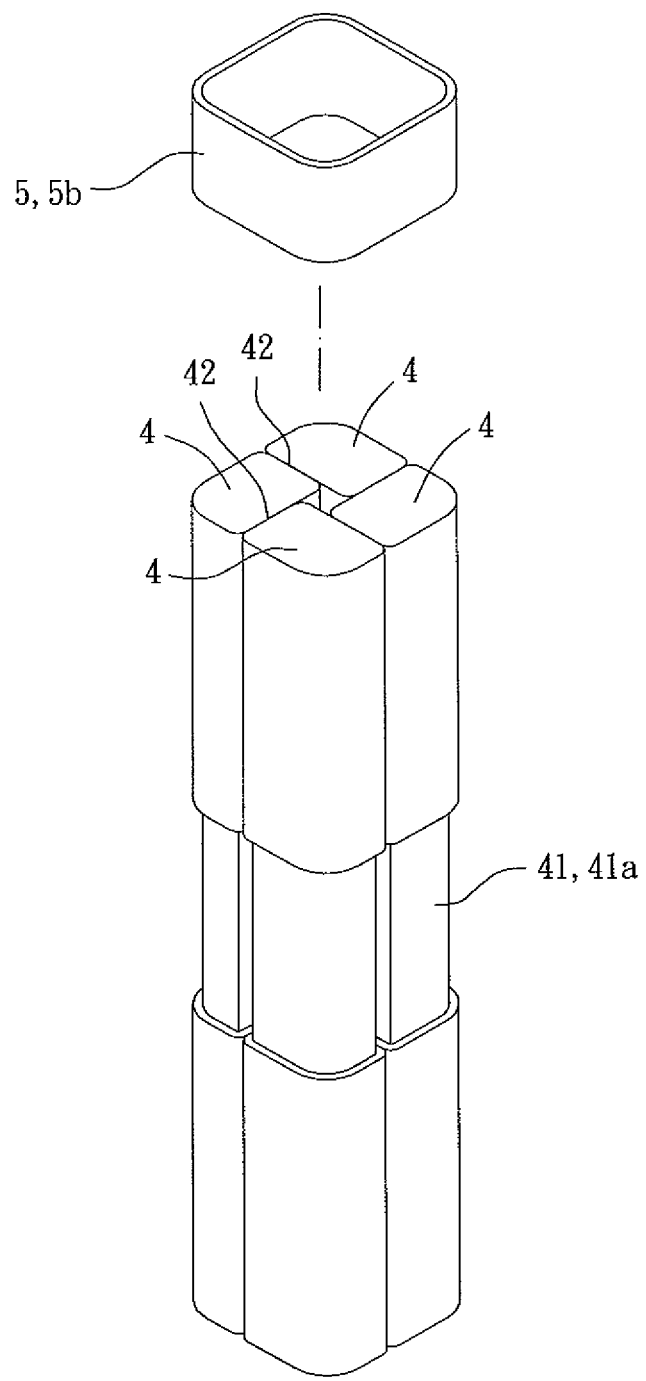
FIG. 16 shows a perspective view of a support instrument with a modular intramedullary nail according to the second embodiment of the invention before assembled by a ring made of shape-memory metal.
Figure 17:
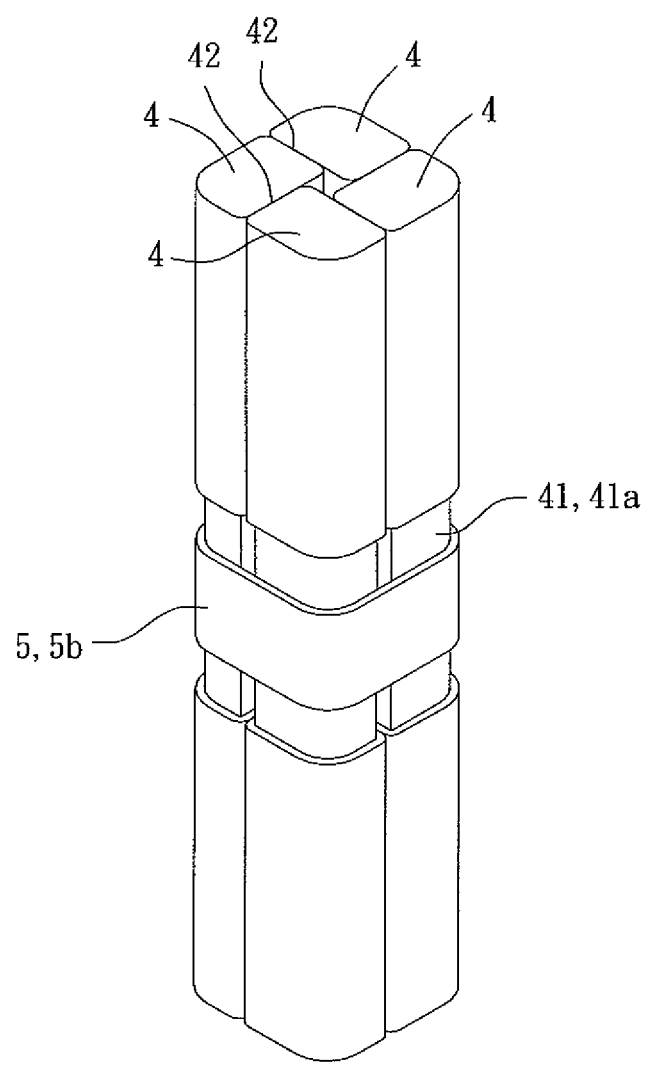
FIG. 17 shows a perspective view of a support instrument with modular intramedullary nail according to the second embodiment of the invention after assembled by the ring made of shape-memory metal.

Referring to FIG. 16, the coupling module 5 can also be of at least one ring 5b made of shape-memory metal, which is usually a nickel-titanium alloy, and the character of the shape-memory metal is that it is deformable in a low temperature and will recover the original shape when the temperature raises back. Referring to FIGS. 16 and 17, when the ring 5b is used, the ring 5b is firstly extended in a low temperature environment to have a large inner diameter to let the assembly of the intramedullary nails 4 pass through the ring 5b. Then, the ring 5b is heated by the body temperature to shrink back to the original size and to firmly clasp the intramedullary nails 4 after the ring 5b surrounds the neck jointly formed by bottoms of the grooves 41a.

Figure 18:
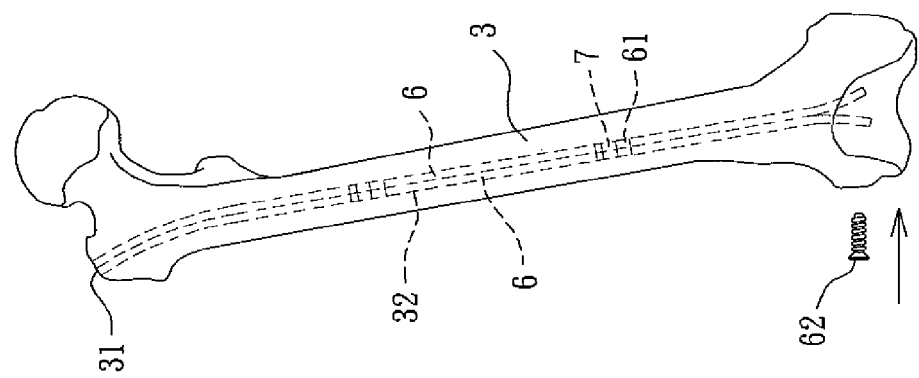
FIG. 18 shows a side view of the support instrument with a modular intramedullary nail according to a third embodiment of the invention of a first step during insertion.
Figure 19:
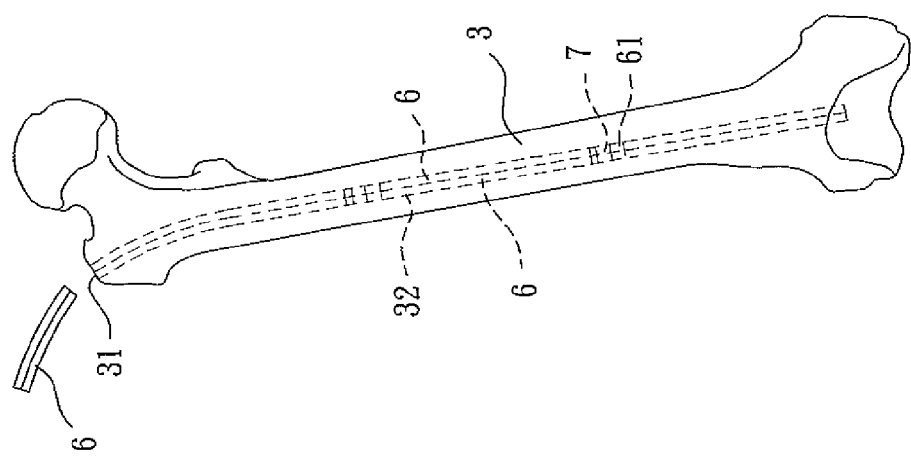
FIG. 19 shows a side view of the support instrument with a modular intramedullary nail according to a third embodiment of the invention of a second step during insertion.
Figure 20:
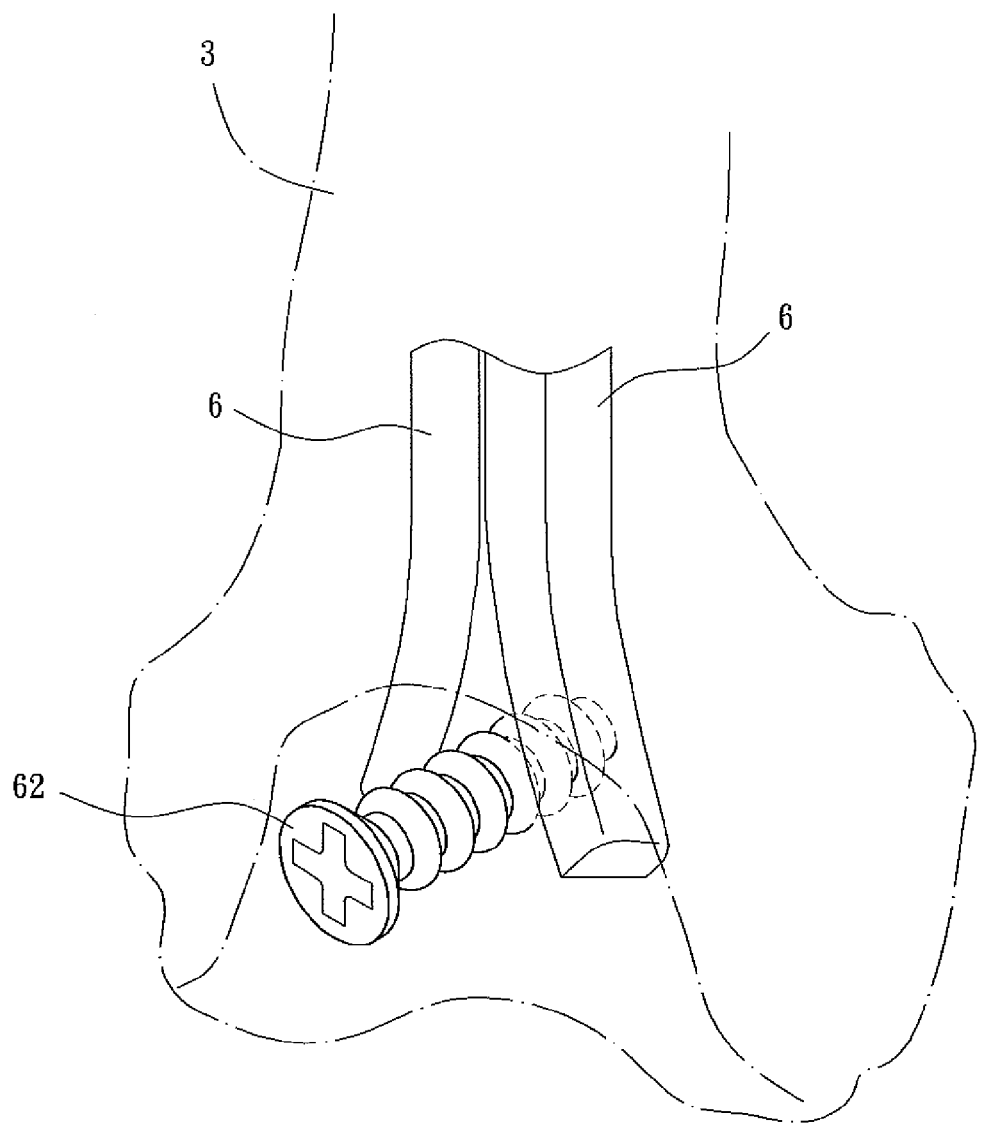
FIG. 20 shows a detailed perspective view of an intramedullary nail according to the third embodiment of the invention.

Referring to FIG. 18, a third embodiment of a support instrument with modular intramedullary nail including a plurality of intramedullary nails 6 and at least one coupling module 7 is shown. The plurality of intramedullary nails 6 and at least one coupling module 7 are in the shapes of those illustrated in the first or second embodiments. Particularly, the plurality of intramedullary nails 6 is made of shape-memory metal, with an end of each intramedullary nail 6 having a curve portion bent relative to other parts of the intramedullary nail 6 through coupling portions 61 thereof. Please further refer to FIG. 19. With the above structure, the curve portions of the plurality of intramedullary nails 6 are set to extend in different directions before the at least one coupling module 7 firmly clasps the plurality of intramedullary nails 6. Referring to FIG. 18 again, before being inserted into the medullary cavity 32 of the long bone 3 through the hole 31 thereof, the curve portions of the plurality of intramedullary nails 6 are initially pulled to extend in the same direction at a low temperature. Further referring to FIG. 19, the plurality of intramedullary nails 6 will be heated by body temperature and the curve portions can be bent in different directions again to firmly abut against the inner surface of the medullary cavity 32. Besides, at least one screw 62 can be inserted into a gap between the curve portions of the plurality of intramedullary nails 6 as shown in FIG. 20 to prevent the support instrument constructed by the plurality of intramedullary nails 6 and at least one coupling module 7 from rotation relative to the inner surfaces of the medullary cavity 32.

Particularly, due to the flexible character of shape-memory metal, the plurality of intramedullary nails 6 can be smoothly inserted into the medullary cavity 32 along the route thereof without bending the plurality of intramedullary nails 6 into a shape matching the route of the medullary cavity 32.

In sum, with the support instrument with a modular intramedullary nail of the present invention, support instruments for supporting bones in different sizes can be provided by a plurality of intramedullary nails 1, 4, 6 having identical dimensions. Therefore, hospitals only need to buy and store identical intramedullary nails 1, 4, 6 for the medical operator to construct a suitable support instrument according to the present situation. Thus, the difficulty in reserve management for hospitals and manufacturers can be largely lowered.

Although the invention has been described in detail with reference to its presently preferable embodiments, it will be understood by one of ordinary skill in the art that various modifications can be made without departing from the spirit and the scope of the invention, as set forth in the appended claims.

What is claimed is:

1. A supporting instrument with a modular intramedullary nail comprising:
   a plurality of intramedullary nails, wherein each intramedullary nail is in a form of a long rod having two ends and a plurality of longitudinal faces, wherein each long rod has a cross section of a rectangular shape and of a constant size between the two ends thereof, with each long rod having a coupling portion and a plurality of abutting surfaces extending along the plurality of longitudinal faces, with the coupling portion arranged between the two ends of the long rod, with the plurality of abutting surfaces comprising a first abutting surface and a second abutting surface connected to each other to form a first corner of the rectangular shape, with a rib and a first groove formed on the first abutting surface, with a second groove formed on the second abutting surface, and with a second corner of the rectangular shape spaced from the first corner being pared off to form a round face; and
   a coupling module mounted to the coupling portions of the plurality of intramedullary nails for the abutting surfaces of the plurality of intramedullary nails to abut against each other and for assembling the plurality of intramedullary nails.

2. The supporting instrument with a modular intramedullary nail as claimed in claim 1, wherein the coupling portion is in a form of a through hole penetrating two opposing longitudinal faces of the plurality of longitudinal faces of each intramedullary nail, and wherein the coupling module is an insertion pin.

3. The supporting instrument with a modular intramedullary nail as claimed in claim 1, wherein the coupling portion is in a form of a groove formed on two opposing longitudinal faces of the plurality of longitudinal faces of each intramedullary nail, and wherein the coupling module is a C-shaped hook or a ring received in the groove.

4. The supporting instrument with a modular intramedullary nail as claimed in claim 3, wherein the ring is made of shape-memory metal.

5. The supporting instrument with a modular intramedullary nail as claimed in claim 3, wherein a width of the C-shaped hook or the ring is smaller than a width of the groove for the C-shaped hook or the ring to firmly couple with.

6. The supporting instrument with a modular intramedullary nail as claimed in claim 1, wherein the rib, the first groove and the second groove on the first and second abutting surfaces are assembled by moving in a direction opposite to a direction in which the rib, the first groove and the second groove extend.

7. The supporting instrument with a modular intramedullary nail as claimed in claim 6, wherein a distal end of the rib away from the first abutting surface is wider than a root end of the rib connecting with the first abutting surface, and wherein a bottom end of the first groove and the second groove is wider than an opening end of the first groove and the second groove at the first and second abutting surfaces.

8. The supporting instrument with a modular intramedullary nail as claimed in claim 1, wherein each intramedullary nail is made of shape-memory metal.

9. The supporting instrument with a modular intramedullary nail as claimed in claim 1, wherein each intramedullary nail has a curve portion at one of the two ends bent relative to another portion extending from the curve portion to another one of the two ends of each intramedullary nail, and wherein the curve portions of the plurality of intramedullary nails extend in different directions to firmly abut against an inner surface of a medullary cavity.

10. The supporting instrument with a modular intramedullary nail as claimed in claim 9, wherein at least one screw is inserted into a gap between the curve portions and spaced from the other portions of the plurality of intramedullary nails.

11. An intramedullary nail comprising:
a body in a form of a long rod having two ends and a plurality of longitudinal faces, wherein the long rod has a cross section of a rectangular shape of a constant size between the two ends thereof, with the long rod having a plurality of abutting surfaces extending along the plurality of longitudinal faces, with the plurality of abutting surfaces comprising a first abutting surface and a second abutting surface connected to each other to form a first corner of the rectangular shape, with a rib and a first groove formed on the first abutting surface, with a second groove formed on the second abutting surface, and with a second corner of the rectangular shape spaced from the first corner being pared off to form a round face; and
a coupling portion arranged between the two ends, with the coupling portion being a through hole or a groove.

12. The intramedullary nail as claimed in claim 11, wherein the coupling portion is in a form of a through hole penetrating two opposing longitudinal faces of the plurality of longitudinal faces of the body, and wherein the coupling module is an insertion pin.

13. The intramedullary nail as claimed in claim 11, wherein the coupling portion is in a form of a groove formed on two opposing longitudinal faces of the plurality of longitudinal faces of the rod, and wherein the coupling module is a C-shaped hook or a ring received in the groove.

\* \* \* \* \*